United States Patent
Marcus et al.

(10) Patent No.: US 9,237,750 B2
(45) Date of Patent: Jan. 19, 2016

(54) ORNIDAZOLE AND RELATED COMPOUNDS FOR USE AS HERBICIDES

(71) Applicant: RAMOT AT TEL-AVIV UNIVERSITY LTD., Tel Aviv (IL)

(72) Inventors: Yehouda Marcus, Jerusalem (IL); Michael Gurevitz, Ra'anana (IL)

(73) Assignee: RAMOT AT TEL-AVIV UNIVERSITY LTD., Tel Aviv (IL)

( * ) Notice: Subject to any disclaimer, the term of this patent is extended or adjusted under 35 U.S.C. 154(b) by 0 days.

(21) Appl. No.: 14/412,801

(22) PCT Filed: Jul. 3, 2013

(86) PCT No.: PCT/IL2013/050565
§ 371 (c)(1),
(2) Date: Jan. 5, 2015

(87) PCT Pub. No.: WO2014/006617
PCT Pub. Date: Jan. 9, 2014

(65) Prior Publication Data
US 2015/0189881 A1    Jul. 9, 2015

Related U.S. Application Data

(60) Provisional application No. 61/667,955, filed on Jul. 4, 2012.

(51) Int. Cl.
*A01N 43/00* (2006.01)
*A01N 43/50* (2006.01)
*A01N 25/04* (2006.01)
*A01N 25/06* (2006.01)
*A01N 25/14* (2006.01)

(52) U.S. Cl.
CPC ............... *A01N 43/50* (2013.01); *A01N 25/04* (2013.01); *A01N 25/06* (2013.01); *A01N 25/14* (2013.01)

(58) Field of Classification Search
None
See application file for complete search history.

(56) References Cited

U.S. PATENT DOCUMENTS

| 3,435,049 A * | 3/1969 | Hoffer .................. 548/330.1 |
| 3,493,582 A | 2/1970 | Hoffer |
| 3,501,286 A | 3/1970 | Draber |
| 4,046,773 A | 9/1977 | Andriska |
| 4,235,995 A | 11/1980 | Jones |
| 5,206,257 A | 4/1993 | Cramp |
| 5,380,865 A | 1/1995 | Cramp |

FOREIGN PATENT DOCUMENTS

| CN | 101455664 | * | 6/2009 |
| CN | 101732242 | * | 6/2010 |
| JP | S 61109701 A | | 5/1986 |

OTHER PUBLICATIONS

Wang et al., The resistant mutant prevention concentrations determination of levornidazole and other three related drugs and analysis to suitability of these drug's dosage in clinic, Yaoxue Jinzhan (2012), 36(6), 277-281.*
Kher et al., Validated LC method for simultaneous analysis of Cefixime and Ornidazole in commercial tablets, International Journal of ChemTech Research (2012), 4(3), 1124-1136.*
Nagavalli et al., RP-HPLC method development and validation for the simultaneous estimation of levofloxacin hemihydrate and ornidazole in tablets, International Journal of PharmTech Research (2009), 1(4), 1161-1163.*
Gandhimathi et al., Validated high performance thin layer chromatography method for simultaneous estimation of ofloxacin and ornidazole in tablet dosage form, Indian Journal of Pharmaceutical Sciences (2006), 68(6), 838-840.*
Zou et al., Formulation stability of cefuroxime and ornidazole injections, Guangdong Yaoxue (2005), 15(4), 56-57.*
Piccolomini et al., In vitro antimycotic activity of an econazole-ornidazole combination (1:10 ratio), Bollettino dell'Istituto Sieroterapico Milanese (1983), 62(3), 257-61.*
Schwartz et al., Comparative pharmacokinetic studies of ornidazole and zole in man, Chemotherapy (Basel, Switzerland) (1976), 22(1), 19-29.*
Ami Ben-Amotz et al "On the Factors Which Determine Massive beta-Carotene Accumulation in the Halotolerant Alga Dunaliella bardawil". Plant Physiol 72(3): 593-7 (1983).
David I. Edwards "Nitroimidazole drugs—action and resistance mechanisms. I. Mechanisms of action". Journal of Antimicrobial Chemotherapy 31(1): 9-20 (1993).
David I. Edwards et al "Metronidazole—an antimicrobial drug which inhibits photosynthesis" Z Pflanzenphysiol 71: S424-427 (1974).
Maya Haimovich et al., "The role of C4 metabolism in the marine diatom Phaeodactylum tricornutum". New Phytol 197(1): 177-85 (2013).
Yehouda Marcus et al., Mutagenesis at two distinct phosphate-binding sites unravels their differential roles in regulation of Rubisco activation and catalysis. J Bacteriol 187(12): 4222-8 (2005).
H Pelicano et al., "Glycolysis inhibition for anticancer treatment. Oncogene" 25(34): 4633-46 (2006).

(Continued)

*Primary Examiner* — Alton Pryor
(74) *Attorney, Agent, or Firm* — Browdy and Neimark, PLLC

(57) ABSTRACT

The present invention relates to the use of Ornidazole and related compounds as herbicides active on a wide range of photoautotrophic organisms. The compounds of the present invention show effective herbicidal activity while being non-hazardous to the environment and to human health.

20 Claims, 7 Drawing Sheets

(56) References Cited

OTHER PUBLICATIONS

U. Schreiber et al. "Continuous recording of photochemical and non-photochemical chlorophyll fluorescence quenching with a new type of modulation fluorometer". Photosynth Res 10(1-2): 51-62 (1986).

Ainit Snir et al., "Alterations in Rubisco activity and in stomatal behavior induce a daily rhythm in photosynthesis of aerial leaves in the amphibious-plant Nuphar lutea". Photosynth Res 90(3): 233-42 (Aug. 2006).

Acgun Trebst "Inhibitors in the functional dissection of the photosynthetic electron transport system". Photosynth Res 92(2): 217-24 (2007).

* cited by examiner

ORNIDAZOLE AND RELATED COMPOUNDS FOR USE AS HERBICIDES

FIELD OF THE INVENTION

The present invention relates to herbicides that are effective in inhibiting the growth of photosynthetic organisms and are essentially not hazardous to the environment and to mammal health.

BACKGROUND OF THE INVENTION

The massive use of synthetic chemical herbicides in modern agriculture has raised public concern over the associated risks to human health and contamination of the environment. In addition, a growing number of herbicide resistant weeds have been observed. There is an ongoing effort to identify and develop herbicides that are active on a wide range of photoautotrophic organisms and that are less hazardous to human health and to the environment.

The photosynthetic apparatus in photoautotrophic organisms including plants, algae and cyanobacteria is a common target for herbicides. This apparatus comprises the light reactions that transform light into chemical energy in the form of ATP and NADPH, and the carbon fixation pathway (Calvin cycle).

Light absorbed by the photosynthetic apparatus is utilized to oxidize and split water into molecular $O_2$ and protons, while the electrons liberated are transferred via an electron transport chain and reduce $NADP^+$ to NADPH. The proton gradient formed across the thylakoid membrane serves as a driving force for ATP formation from ADP and phosphate by the membrane enzyme ATP synthase. Several known herbicides are targeted to various sites in the electron transport chain; for example DCMU (Diuron) or Atrazine inhibit electron transfer between two quinones associated with photosystem II, and Methyl viologen (Paraquat) that accepts electrons from photosystem I, thereby producing reactive oxygen species that destroy the photosynthetic apparatus (Trebst A. 2007. *Photosynth Res* 92:217-224).

The Calvin cycle may be roughly divided to three stages: (1) Carboxylation of ribulose-1,5-bisphosphate (RuBP), a reaction catalyzed by RuBP carboxylase/oxygenase (Rubisco), resulting in the generation of 3-phosphoglycerate (PGA); (2) PGA reduction to glyceraldehyde-3-phosphate (GA3P). The PGA reduction occurs in two consecutive reactions catalyzed by phosphoglycerate kinase and GA3P dehydrogenase (GAPDH) using ATP and NADPH produced in the light reactions. GA3P is isomerized by triose phosphate isomerase to dihydroxyacetone phosphate (DHAP). These two triose phosphates, GA3P and DHAP, are substrates for the production of all carbohydrates and organic matter thereof; and (3) Recycling of RuBP from triose phosphates in a series of reactions. To the best ability of the inventors to ascertain, no herbicide capable of penetrating the cell membrane and targeting the Calvin cycle has thus far been reported.

Several enzymes including Rubisco and phosphoribulose kinase act exclusively in the Calvin cycle; yet, isozymes similar to most of the Calvin cycle enzymes function also in the glycolytic and gluconeogenic pathways. Although inhibitors of glycolysis and gluconeogenesis that are used as anti metabolic drugs in cancer and infectious diseases have been reported (Pelicano et al., 2006. *Oncogene* 25:4633-4646), no selective inhibitor of the Calvin cycle that is able to penetrate into cells of photosynthetic organisms has been documented.

Nitroimidazole derivatives, particularly 4 (or 5)-nitroimidazole derivatives have been long reported as useful in the treatment of infections caused by pathogenic protozoa including, for example certain species of amoebae (U.S. Pat. Nos. 3,435,049 and 3,493,582).

Additional nitroimidazole derivatives were reported as effective fungicides and anti-bacterial agents that may be used as pharmaceuticals as well as pesticides. For example, U.S. Pat. No. 4,046,773 discloses carbamoyl-imidazole derivative having pesticide activity, which may be also used as an herbicide.

U.S. Pat. Nos. 5,206,257 and 5,380,865 discloses 2-phenylimidazole derivatives that can be used for the control of arthropod, plant nematode, helminth or protozoan.

U.S. Pat. No. 4,235,995 discloses the production of 1,4-disubstituted-3-nitropyrazoles having antimicrobial, parasiticidal, and herbicidal activity. Preferred compounds are 1-alkyl or -alkenyl-4-pyrazolecarboxamides are carbonitriles. The new compounds are particularly useful for the control of bacterial animal diseases.

Japanese Patent Application Publication No. 61109701 discloses herbicide containing 2-methyl-4(5)-trifluoromethyl-5(4)-nitroimidazole as an active ingredient. The herbicide is effective on a wide range of weeds and may be used by soil treatment, foliar treatment or treatment under flooding condition as pre- or post-emergence treatment.

Edwards et al. (Edwards D I et al. 1974, Z. Pflanzenphysiol. Bd. 71:S424-427) showed that Metronidazole (1-β-hydroxyethyl-2-methyl-5-nitroimidazole), known as an antimicrobial drug, is effective in inhibiting the photosynthetic electron transport. Metronidazole was shown to act as a potent inhibitor of ferredoxin-linked $NADP^+$ reduction in a system in which photosystem II is non-operative and ascorbate acts as an electron source. The system included $NADP^+$, broken spinach chloroplasts, intermediate electron carrier (DCPIP) and ferredoxin.

Ornidazole (1-chloro-3-(2-methyl-5-nitro-1H-imidazol-1-yl)propan-2-ol) is known as an anti bacterial and anti protozoan drug. Recently, it has been elucidated that Ornidazole inhibits the activity of the glycolytic enzymes glyceraldehyde-3-phosphate dehydrogenase (GAPDH) and triose phosphate isomerase (Pelicano et al., 2006, ibid). Ornidazole is widely used in treating bacterial and protozoa infection in poultry and in mammals, including humans.

There is a recognized ongoing need for effective herbicides with wide range activity that are not hazardous to the environment and are not harmful to mammals.

SUMMARY OF THE INVENTION

The present invention relates to the use of Ornidazole and compounds related thereto as herbicides. This herbicide has the advantage of being biodegradable.

The present invention is based in part on the unexpected discovery that Ornidazole significantly inhibits photosynthesis while having only minor effect on respiration of photoautotrophic organisms. Without wishing to be bound by any specific theory or mechanism of action, this differential inhibition may be attributed to significant inhibition of enzymes involved in the Calvin cycle, particularly inhibition of the Calvin cycle triose phosphate isomerase, but not of its isoenzymes involved in respiration.

Thus, according to one aspect, the present invention provides a method of inhibiting growth of photosynthetic organisms, the method comprises applying to the organism and/or to its habitat a compound or plurality of compounds having the general formula I, or a salt thereof:

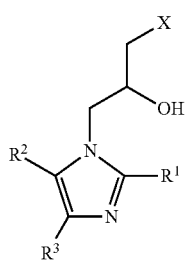

wherein:
$R^1$ is H, halogen or $C_1$-$C_4$ alkyl;
one of $R^2$ and $R^3$ is H or halogen and the other is $NO_2$; and
X is a halogen, thereby inhibiting the growth of said organism.

According to certain embodiments, $R^1$ is $C_1$-$C_4$ alkyl. According to certain embodiments, $R^1$ is methyl.

According to other embodiments, the halogen is selected from the group consisting of fluorine, chlorine, bromine and iodine. According to certain embodiments, the halogen is chlorine.

According to certain embodiments, the compound is Ornidazole, wherein $R^1$ is methyl, $R^2$ is $NO_2$, $R^3$ is H and X is chlorine, or a salt thereof.

According to certain embodiments, the photosynthetic organism is selected from the group consisting of plants, algae and cyanobacteria. According to some embodiments, the plants are selected from aquatic and terrestrial plants. According to other embodiments, the algae are selected from green algae and diatoms. Each possibility represents a separate embodiment of the present invention.

It is to be understood that compounds having formula I may be used to control the growth of photosynthetic organisms in certain habitats. Accordingly, the compound or plurality of compounds having formula I are referred to herein as herbicidal compound or compounds.

The herbicidal compounds having formula I according to the teachings of the present invention can be applied to the photosynthetic organism, a part thereof or its habitat by any method as is known to a person skilled in the art.

According to certain embodiments, when the photosynthetic organism is a terrestrial plant, the Ornidazole compound or compounds related thereto are applied to the aerial part of the plant. According to other embodiments, the compounds are applied to the plant roots. According to certain embodiments the Ornidazole or Ornidazole related compounds is applied shortly after seed emergence.

According to additional embodiments, the herbicidal compound or compounds having formula I are applied to the photosynthetic organism habitat. According to certain embodiments the herbicidal compounds are applied to the photosynthetic organism growth medium, wherein the medium is selected from the group consisting of solid growth medium and aquatic growth medium. According to some embodiments, the solid medium is natural soil. According to other embodiments, the solid medium is artificial soil.

The Ornidazole and Ornidazole related compounds according to the teachings of the present invention can be formulated as herbicidal composition, further comprising an agriculturally acceptable diluents or carrier. The form of formulation is designed according to the type of the photosynthetic organism and the method of application, as is known to a person skilled in the art. According to certain embodiments, the composition further comprises at least one additional active ingredient selected from the group consisting of fungicides, insecticides, additional herbicides, nematicides, acaricides, bactericides, plant growth regulators, fertilizers, soil improvers or a combination thereof.

According to certain embodiments, the compound having formula I or a plurality of such compounds is applied at a total concentration of from about 0.2 mM to about 5 mM, typically at a concentration of from about 0.5 mM to about 2.0 mM.

Other objects, features and advantages of the present invention will become clear from the following description and drawings.

DETAILED DESCRIPTION OF THE INVENTION

Figure 1:
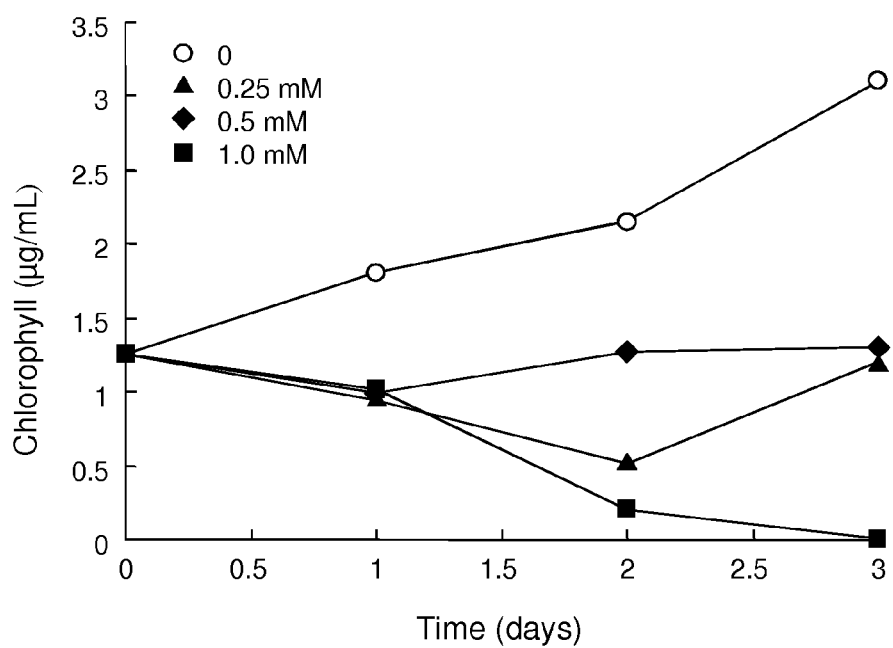
FIG. 1 shows the effect of Ornidazole on the growth of the cyanobacterium Anabaena PCC7120 as reflected by the chlorophyll concentration. Cyanobacteria were grown in BG11 medium under 30 µmol photons $m^{-2}$ $sec^{-1}$ at 30° C. in the presence of the indicated concentration of Ornidazole.

The present invention discloses for the first time that Ornidazole and Ornidazole related compounds can be used as efficient and safe herbicides, based on the unexpected finding that these compounds significantly inhibit photosynthesis while having only minor effect on respiration in photosynthetic organisms. These Ornidazole-related compounds thus specifically inhibit or abolish the growth of photosynthetic organisms but are not hazardous to the environment or to human health. Furthermore, Ornidazole and the Ornidazole related compounds are biodegradable, thus having minimal effect on the environment.

Definitions

The terms "photosynthetic organism" or "photoautotrophic organism" are used herein in their broadest aspect referring to any organism capable of using light energy for inorganic carbon fixation, employing, inter alia, the Calvin cycle. In the teachings of the present invention, the growth of the photosynthetic organism in a particular habitat is undesired, and thus should be inhibited or eliminated. Thus, the photosynthetic organism may be defined as a weed.

The terms "compound or compounds having formula I" "Ornidazole and compounds related to Ornidazole" and "herbicidal compound or compounds" are used herein interchangeably, and refer to a compound or plurality of compounds having the general formula I, with Ornidazole being a typical embodiment.

The terms "plant" or "plants", "alga" or "algae" and "cyanobacterium" or cyanobacteria are used herein in their broadest sense, and include the organism and any part thereof, including the organism dispersal units. It also refers to a plurality of the organism cells that are largely differentiated into a structure that is present at any stage of the organism's development. When the photosynthetic organism is a plant, such structures include, but are not limited to, a root, stem, shoot, leaf, flower, petal, fruit, etc. It is to be explicitly understood that the term "plant" also encompasses plant seeds.

As used herein the term "habitat" refers to the physical environment wherein the photosynthetic organism grows and in particular to the growth medium of the photosynthetic organism. The habitat greatly depends on the type of the photosynthetic organism; growth media include any medium that supports the growth of plants, algae or cyanobacteria, including, but not limited to, various types of soils or aqueous media.

A "$C_1$-$C_4$ alkyl" group refers to a saturated aliphatic hydrocarbon comprising one to four carbon atoms, including straight-chain or branched-chain structures. Examples include methyl, ethyl, propyl, isopropyl, n-butyl, isobutyl, sec-butyl and t-butyl, with each possibility representing a separate embodiment of the present invention.

The term "halogen" or "halo" as used herein alone or as part of another group refers to chlorine, bromine, fluorine, and iodine.

One or more of the compounds used in the present invention, may be present as a salt. The term "salt" encompasses both basic and acid addition salts.

According to one aspect, the present invention provides a method of inhibiting the growth of photosynthetic organism, comprising applying to the organism or its habitat a compound or plurality of compounds having the general formula I:

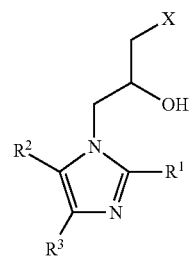

wherein:
$R^1$ is H, halogen or $C_1$-$C_4$ alkyl;
one of $R^2$ and $R^3$ is H or halogen and the other is $NO_2$; and
X is a halogen.

According to certain embodiments, $R^1$ is $C_1$-$C_4$ alkyl. According to certain embodiments, $R^1$ is methyl.

According to other embodiments, the halogen is selected from the group consisting of fluorine, chlorine, bromine and iodine. According to certain embodiments, the halogen is chlorine.

According to certain embodiments, the compound is Ornidazole, wherein $R^1$ is methyl, $R^2$ is $NO_2$, $R^3$ is H and X is chlorine, or a salt thereof.

The Ornidazole or its related compounds according to the teachings of the present invention may be used as such or may be formulated as an herbicidal composition. There is no specific limitation for formulation of the herbicidal composition of the invention, as far as the composition contains a compound or plurality of compounds having formula I as an active ingredient.

The formulations generally comprise between 0.1 and 95 percent by weight of active compound, preferably between 0.5 and 90%.

According to certain embodiments, the composition further comprises at least one of carriers, diluents, emulsifying agents, surface active agents, dispersants, adjuvants and the like, as is known to a person skilled in the art. The herbicidal composition can be used as any of generally adoptable formulations of agricultural chemicals, such as wettable powders, granules, powders, dusts, pastes, emulsions, water-soluble powders, suspensions, solutions, aerosols and flowable compositions, impregnated with natural and synthetic substances and microencapsulated in polymeric substances.

Examples of the solid carriers or diluents include plant substances, fibrous materials, synthetic plastic powders, clays (e.g., kaolin, bentonite, terra abla), talc or inorganic materials (pumice, powdered sulfur). Examples of the liquid carriers or diluents include water, alcohols, ketones, ethers, aromatic hydrocarbons, aliphatic hydrocarbons, esters, nitrites, amides (N,N-dimethylformamide, dimethyl sulfoxide), and halogenated hydrocarbons.

If the diluent used is water, it is also possible to use, for example, organic solvents as auxiliary solvents. Liquid solvents which are mainly suitable are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide.

Suitable solid carriers are for example, ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are for example, crushed and fractionated natural rocks, such as calcite, marble, pumice, sepiolite, dolomite and synthetic granules of inorganic and organic meals, and granules of organic material, such as sawdust, coconut shells, maize cobs and tobacco stalks; suitable emulsifiers and/or foam formers are for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are for example, lignosulphite waste liquors and methylcellulose.

Tackifiers, such as carboxymethylcellulose, natural and synthetic polymers in the form of powders, granules or latices, such as gum arabic, polyvinyl alcohol and polyvinyl acetate, and also natural phospholipids, such as cephalins and lecithins, and synthetic phospholipids can be used in the formulations. Other possible additives are mineral and vegetable oils.

It is possible to use dyestuffs, such as inorganic pigments, for example iron oxide, titanium oxide, Prussian blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc. Examples of surface active agents include alkylsulfuric acid esters, alkyl sulfonates, polyethylene glycol ethers and polyhydric alcohol esters. Examples of spreaders or the dispersants include casein, gelatin, starch, caboxymethyl cellulose, gum arabic, alginic acid, lignin, bentonite, polyvinyl alcohol, pine oil, molasses and agar.

Examples of stabilizers include isopropylphosphate mixture, tricresyl phosphate, tall oil, epoxy oil, surface active agents, fatty acids and the esters thereof.

According to certain embodiments, the herbicidal composition further comprises at least one additional active agent selected from the group consisting of fungicides, insecticides, additional herbicides, nematicides, acaricides, bactericides, plant growth regulators, fertilizers, soil improvers or a combination thereof.

According to certain embodiments, the photosynthetic organism is selected from the group consisting of plants, algae and cianobacteria. According to some embodiments, the plants are selected from aquatic and terrestrial plants. According to other embodiments, the algae are selected from green algae and diatoms. Each possibility represents a separate embodiment of the present invention. The compounds of the present invention are active in inhibiting any species of plant, alga or cyanobacterium having photosynthetic activity.

The herbicidal compounds having formula I or a composition comprising same may be applied directly onto the photosynthetic organism or part thereof or to its environment, habitat or storage area according to customary treatment methods, for example by dipping, spraying, evaporating, atomizing and brushing-on.

According to certain embodiments, the herbicidal compounds or a composition comprising same are applied to the growth medium of the photoautotrophic organism. Application can be to the surface of the growth medium or the herbicidal compounds can be mixed with the growth medium. As described hereinbaove, the growth medium can be solid, particularly soil, natural or artificial or the growth medium can be liquid, particularly aqueous medium, natural or artificial. Application to the growth medium can be performed in the presence or the absence of the photoautotrophic organism.

In the embodiments wherein the photosynthetic organism is a plant, the compound or compounds having the general formula I or the composition comprising same can be applied before or after emergence of the plant.

According to other embodiments, the herbicidal compounds having formula I or a composition comprising same are applied onto the photosynthetic organism. According to some embodiments the photosynthetic organism is a plant or an alga. When the photosynthetic organism is a plant, application can be, without limitation, onto the plant roots, rhizomes, shoots, foliage, flowers, fruit, seeds, tubers, cuttings or any portion thereof. Each possibility represents a separate embodiment of the present invention.

Applying the herbicidal compound having formula I or the composition comprising same to the foliage of the plant can be carried out by spraying, including high or low pressure spraying. Alternatively, the application is performed by infiltration, including by injection.

It is to be explicitly understood that the compound or plurality of compounds having formula I or the composition comprising same can also be applied using other suitable application procedures as are known to those skilled in the art, provided these procedures are able to effect contact of the herbicidal compounds to the photosynthetic organism, as well as to its dispersal units. According to certain embodiments, the herbicidal compounds or the composition comprising same are applied both onto the photosynthetic organism and to its growth medium.

The effective amount of the compound or plurality of compounds having formula I depends on the photosynthetic organism type, its habitat and its density, as well as on environmental factors including meteorological conditions and growth medium conditions, the formulation type, application method, application time etc. Determining the effective amount for particular conditions is well within the knowledge of a person skilled in the art. According to certain embodiments, the effective concentration of the Ornidazole compound having formula I is in the range of 0.2 mM to 5.0 mM, typically in the range of 0.5 mM to 2.0 mM.

As exemplified herein below, Ornidazole significantly inhibits photosynthesis while having only moderate impact on respiration in the photosynthetic organisms. Without wishing to be bound by any specific theory or mechanism of action, this activity may be attributed to the inhibition of Calvin cycle enzymes by Ornidazole, particularly the inhibition of GAPDH and/or triose phosphate isomerase.

Ornidazole degrades slowly in aqueous solutions. A degradation product resulting from hydrolysis of the chlorine atom is detectable in the solution by LC-MS after a few days. In the presence of Cyanobacteria this degradation is accelerated, thereby reducing the putative environmental risk. The fast effect on photosynthesis (minutes) and moderate biodegradation rate (days) is valuable for using Ornidazole as an herbicide.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Materials and Methods

Growth Conditions:

The cyanobacterium *Anabaena* PCC7120 was grown in BG-11 medium as was previously described (Marcus Y, et al., 2005. J Bacteriol 187, 4222-4228). The green eukaryotic alga *Dunaliella salina* was grown on a medium described by Ben-Amotz and Avron (Ben-Amotz A and Avron M 1983. Plant Physiol 72, 593-597), under 20 µmol photons $m^{-2}$ $sec^{-1}$ at 30° C. The aquatic plant *Lemna* was collected from an open pond at the Botanical garden of Tel Aviv University. Seedlings of *Avena sterilis* were grown in pots in a greenhouse. The marine diatom *Phaeodactylum tricornutum* was grown as described in Haimovich-Dayan et al. (Haimovich-Dayan M. et al. 2012. New Phytol 195:177-185).

Photosynthetic Measurements:

The rate of net $O_2$ exchange was determined using a Clark-type $O_2$ electrode (Rank Brothers Ltd, UK). Fluorescent measurements (quantum yield, photochemical and non photochemical quenching) were determined using a modulated fluorometer (PAM, Walz, Germany) as described by Schreiber et al. (Schreiber U et al., 1986. fluorometer. Photosynth Res 10, 51-62) and Snir et al. (Snir A, et al., 2006. Photosynth Res 90, 233-242).

Spheroplast Preparation:

Filaments of *Anabaena* PCC7120 were incubated in a medium containing: 0.5 M sucrose, 10 mM $MgCl_2$, 5 mM Potassium Phosphate, 10 mM MES buffer pH 6.9, 1% (weight/volume) BSA and 1 mg/ml Lysozyme for 30 to 60 min. at 30° C. The spheroplasts yield was monitored by lysis in hypotonic solution. The spheroplasts were spun down and resuspended in a medium containing 0.4 M Mannitol, 10 mM $MgCl_2$, 5 mM Potassium Phosphate and 20 mM Hepes buffer pH 8.0.

Enzymatic Assays:

Rubisco was assayed as described by Marcus et al. (2005, ibid) and Snir et al. (2006, ibid). Phospho-ribulose kinase was assayed by conversion of phospho-ribulose to RuBP, which was determined by Rubisco dependent carboxylation with radiolabeled $^{14}CO_2$. Plant or cyanobacterial extract was incubated with medium containing 50 mM Hepes pH 8, 10 mM $MgCl_2$, 20 mM $NaH^{14}CO_3$, 1 mM DTT, 0.5 mM ribose-5-phosphate, ribose-5-phosphate isomerase and activated Rubisco. Phosphoglycerate kinase, GAPDH, FBPase and SBPase were determined as described by Leegood (Leegood R C., 1990. In: Methods in plant biochemistry, Vol 3, pp 15-37, Academic Press).

Example 1

Effect of Ornidazole on Photosynthesis and Respiration of Algae

The algae *Anabaena* PCC7120 (Cyanobacteria), *Dunaliella salina* (Chlorophyta) and *Phaeodactylum tricornutum* (Diatoms) were each grown in its suitable medium as described hereinabove towards the mid logarithmic phase. 1 mM Ornidazole was then added to the medium for 5 min, and respiration and photosynthesis were measured for at least 10 min.

Rate of photosynthesis of these photosynthetic organisms was inhibited to various degrees (Table 1). Higher concentrations or longer incubation time with Ornidazole abolished photosynthesis. The effect of Ornidazole on respiration was moderate: Ornidazole at a concentration of 1 mM inhibited the respiration rate of *Anabaena* and *Dunaliella* by only 30-35%; surprisingly, same Ornidazole concentration stimulated the respiration rate of *Phaeodactylum* (Table 1).

TABLE 1

The effect of Ornidazole on photosynthesis and respiration of algae

| Organism | Photosynthesis (µmol $O_2$ $mg^{-1}$ chl $h^{-1}$) | | Respiration (µmol $O_2$ $mg^{-1}$ chl $h^{-1}$) | |
| --- | --- | --- | --- | --- |
| | Control | Ornidazole (1 mM) | Control | Ornidazole (1 mM) |
| *Anabaena* PCC7120 (Cyanobacteria) | 120 | −3.7 | −41.3 | −26.5 |
| *Dunaliella salina* (Chlorophyta) | 42.9 | 17.88 | −4.45 | −3.13 |
| *Phaeodactylum tricornutum* (Diatomea) | 16.34 | −4.33 | −36.9 | −67.14 |

Example 2

Effect of Ornidazole on Growth and Photosynthesis

The effect of Ornidazole on the growth of the cyanobacterium *Anabaena* PCC7120 was examined by determining the chlorophyll concentration. The algae were grown in BG-11 medium as described herein above. Incubation in the presence of 250 µM Ornidazole stopped the growth and stimulated chlorosis of the *Anabaena* cells. One mM Ornidazole in the medium caused a decrease in chlorophyll concentration to 1% of its original concentration after three days of such incubation (FIG. 1).

Figure 2A:
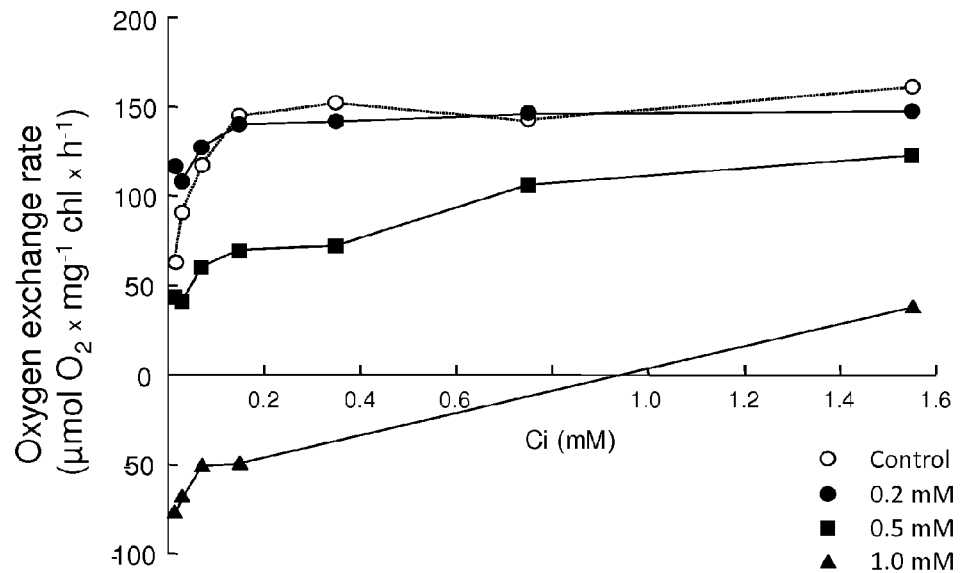
FIG. 2 demonstrates the effect of Ornidazole on the rate of photosynthesis of Anabaena PCC7120 under various concentrations of inorganic carbon and saturating light intensity (FIG. 2A) and under various light intensities and saturating concentration of inorganic carbon (FIG. 2B).
Figure 2B:
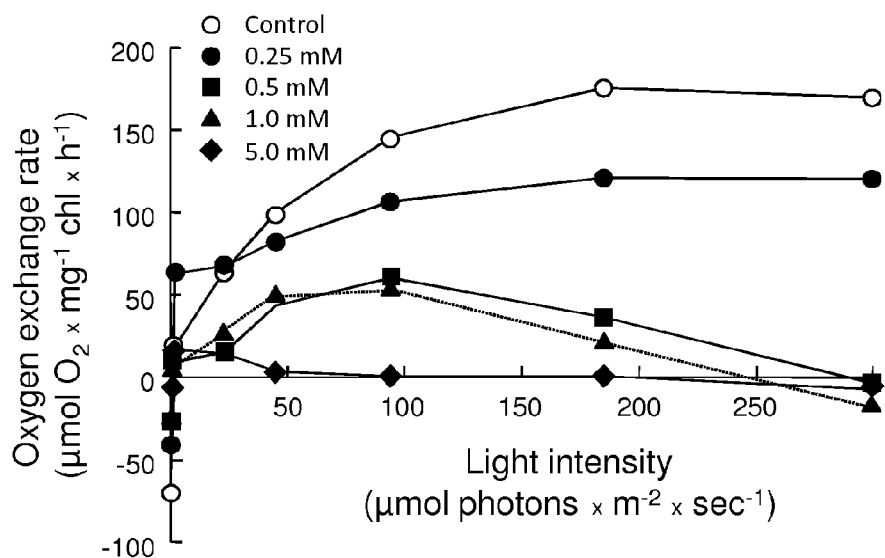
Figure 3:
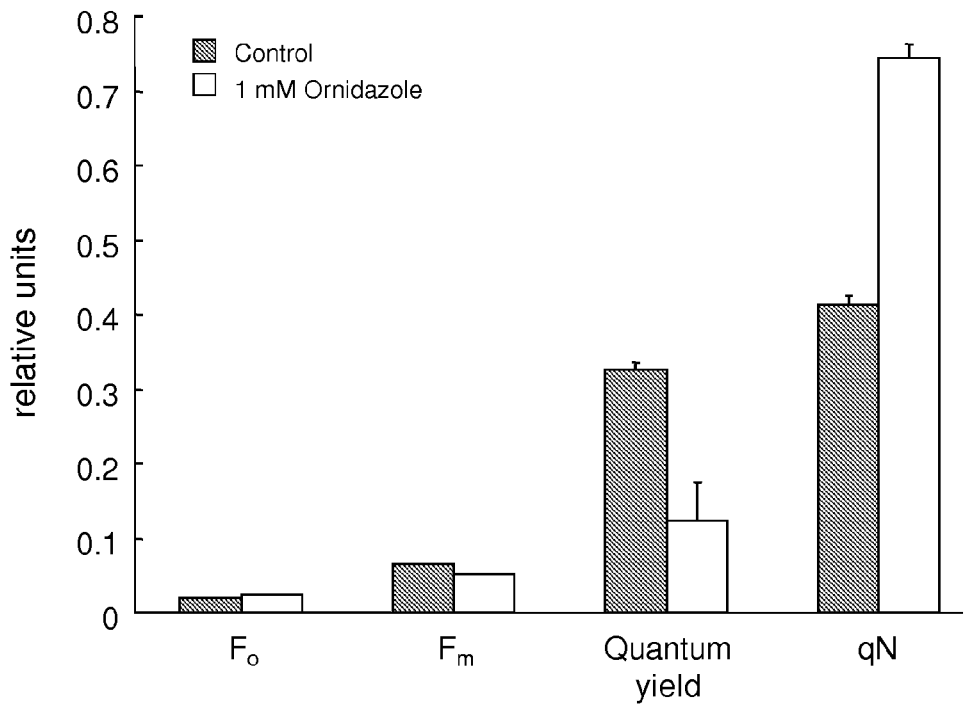
FIG. 3 shows the effect of Ornidazole on fluorescence parameters of the aquatic angiosperm Lemna. The fluorescence under dim (3 µmol photons×$m^{-2}$×$sec^{-1}$) and saturating (2000 µmol photons×$m^{-2}$×$sec^{-1}$, 0.8 sec) flash light ($F_o$ and $F_{max}$, respectively) of pre-darkened plants was determined in the presence or absence of 1 mM Ornidazole in the growth medium, using a PAM fluorimeter. Quantum yield and non-photochemical quenching (qN) were determined with saturating flashes under actinic light (210 µmol photons×$m^{-2}$×$sec^{-1}$).

The effect of Ornidazole on the rate of photosynthesis of *Anabaena* was also determined. The algae were grown under various light intensities and saturating inorganic carbon (Ci) concentration, or under various Ci concentrations and saturating irradiance. The main effect of Ornidazole was a concentration-dependent decrease in the photosynthetic rate under saturating irradiance at any Ci concentration, whereas under limiting irradiance Ornidazole inhibited the photosynthetic rate to a lesser extent (FIG. 2).

The effect of Ornidazole on photosynthesis was further examined in the aquatic plant *Lemna*. *Lemna* plants were collected from a pond at the Botanical garden of Tel Aviv University and kept in the pond water as a growth medium. The fluorescence under dim (3 µmol photons $m^{-2}$ $sec^{-1}$) and saturating (2000 µmol photons $m^{-2}$ $sec^{-1}$, 0.8 sec) flash light ($F_o$ and $F_{max}$, respectively) of pre-darkened plants was determined in the presence or absence of 1 mM Ornidazole in the growth medium, using a PAM fluorimeter (H. Walz, Germany). The quantum yield and non-photochemical quenching were determined with saturating flashes provided under actinic light (210 µmol photons×$m^{-2}$×$sec^{-1}$) as described in Schreiber et al. (ibid)) and Snir et al. (ibid). In the presence of Ornidazole, the photosynthetic quantum yield decreased significantly while the non-photochemical quenching increased.

Figure 4:
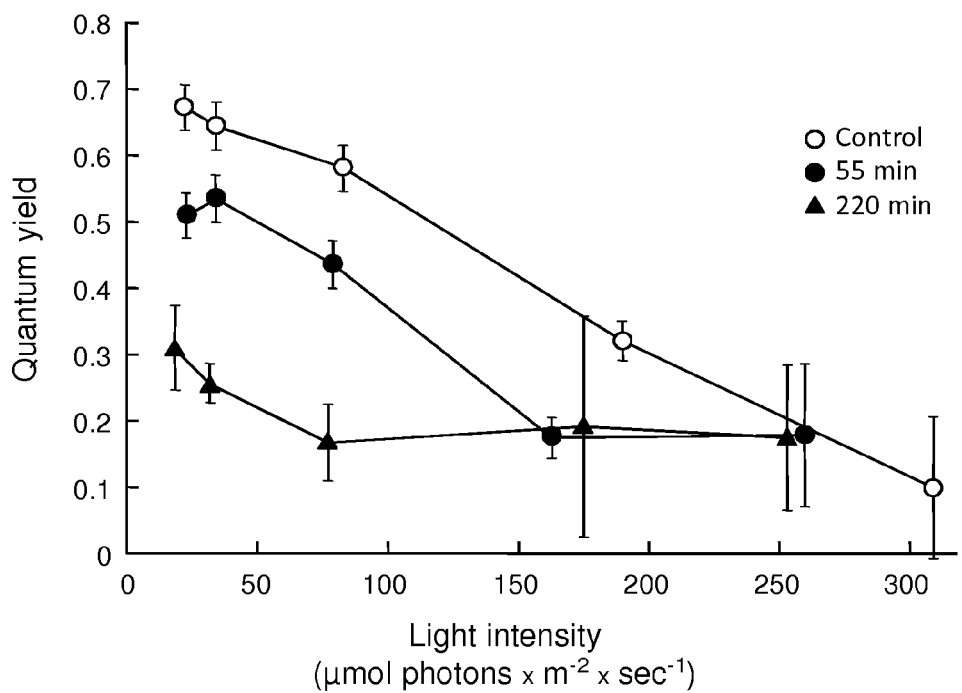
FIG. 4 shows the effect of Ornidazole on the photosynthetic quantum yield of Avena sterilis. Leaves of Avena seedlings grown in a pot (still attached to the stem) were immersed in 1 mM Ornidazole for the indicated times. The photosynthetic quantum yield under various light intensities was determined with a PAM fluorimeter.

Similar results were obtained by immersion of leaf blades of the weed *Avena sterilis* in 1 mM Ornidazole in water. After 3.5 hours of incubation the quantum yield of photosynthesis decreased by 50% under limiting light intensity and by 85% under saturating light intensity (FIG. 4). These results show that Ornidazole inhibits a wide range of photosynthetic organisms.

Example 3

Effect of Ornidazole on Components of the Photosynthetic Apparatus

Figure 5:
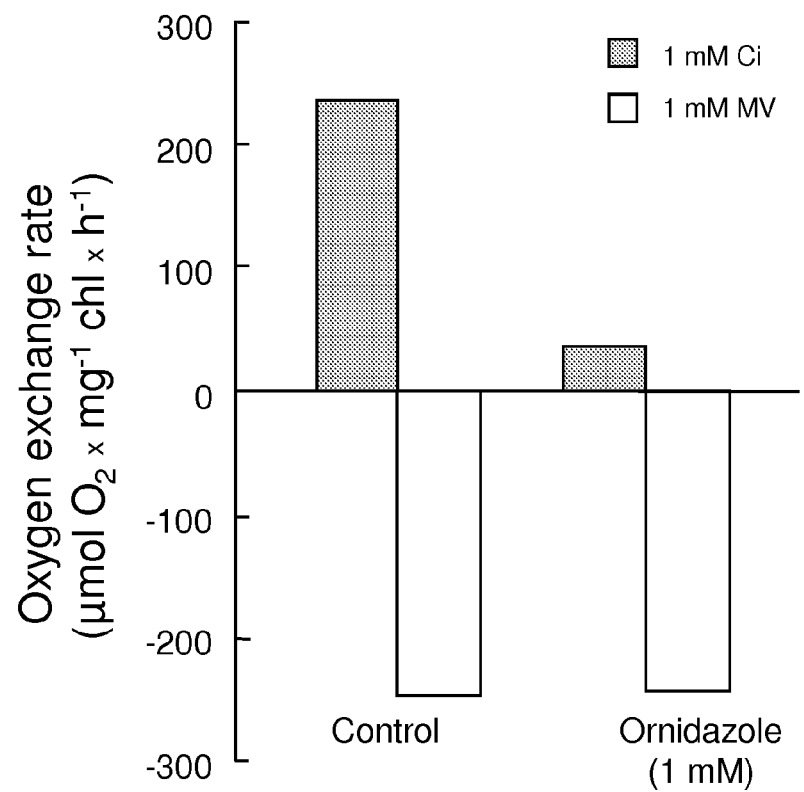
FIG. 5 demonstrates the effect of Ornidazole on photosynthesis and electron transport rates of Anabaena PCC7120. The rates were determined for cells grown in a growth medium at 30° C. under 180 µmol photons×$m^{-2}$×$sec^{-1}$. The rate of electron transport from $H_2O$ via reaction centers II and I and Methyl viologen to $O_2$ was determined in the presence of 1 mM methyl viologen using an $O_2$ electrode.

The effects of Ornidazole on the dark and light reactions of the photosynthetic apparatus were examined. Ornidazole had no effect on the photosynthetic electron transport in *Anabaena* measured from water as electron donor through the two reaction centers to Methyl viologen and finally to oxygen as an electron acceptor (FIG. 5).

However, analysis of Ornidazole effect on various enzymes of the Calvin cycle in *Anabaena* including ribulose-bisphosphate carboxylase/oxygenase (Rubisco), phosphoglycerate kinase, glyceraldehyde-3-phosphate dehydrogenase (GAPDH), triose-phosphate isomerase, aldolase, fructose and sedoheptulose bisphosphatase and phosphoribulose kinase, has shown inhibition of GAPDH and triose-phosphate isomerase (Table 2).

TABLE 2

The effect of Ornidazole on Calvin Cycle enzyme activities

| Enzyme | Activity ($\mu mol \times mg^{-1} chl \times h^{-1}$) | |
|---|---|---|
| | Control | 1 mM Ornidazole |
| Rubisco | 57.9 | 74.6 |
| Phosphoribulose kinase | 34.5 | 66.7 |
| Phosphglycerate kinase | 55.6 | 57 |
| Fructose bisphosphatase | 73.8 | 71 |
| Sedoheptulose bisphosphatase | 65 | 62 |
| Triose phosphate isomerase | 280 | 0 |
| GAPDH | 128 | 1.77 |
| Aldolase | 94.4 | 120 |

The most significant effect of Ornidazole on Calvin cycle enzyme activities was observed for GAPDH and triose-phosphate isomerase, whose activities were inhibited to an extent of 98%-100%.

To further examine the effect of Ornidazole on these enzymes, the rate of photosynthesis of *Anabaena* spheroplasts, incubated in a spheroplast medium under saturating light intensity and $CO_2$ concentrations in the presence of 0 to 2 mM Ornidazole at 30° C. was determined, using an $O_2$ electrode. GAPDH and triose-phosphate isomerase activities were determined spectrophotometrically in the spheroplasts upon lysis (200 to 300 μg chlorophyll) using a reaction medium as described in the Materials and Methods section hereinabove.

Figure 6:
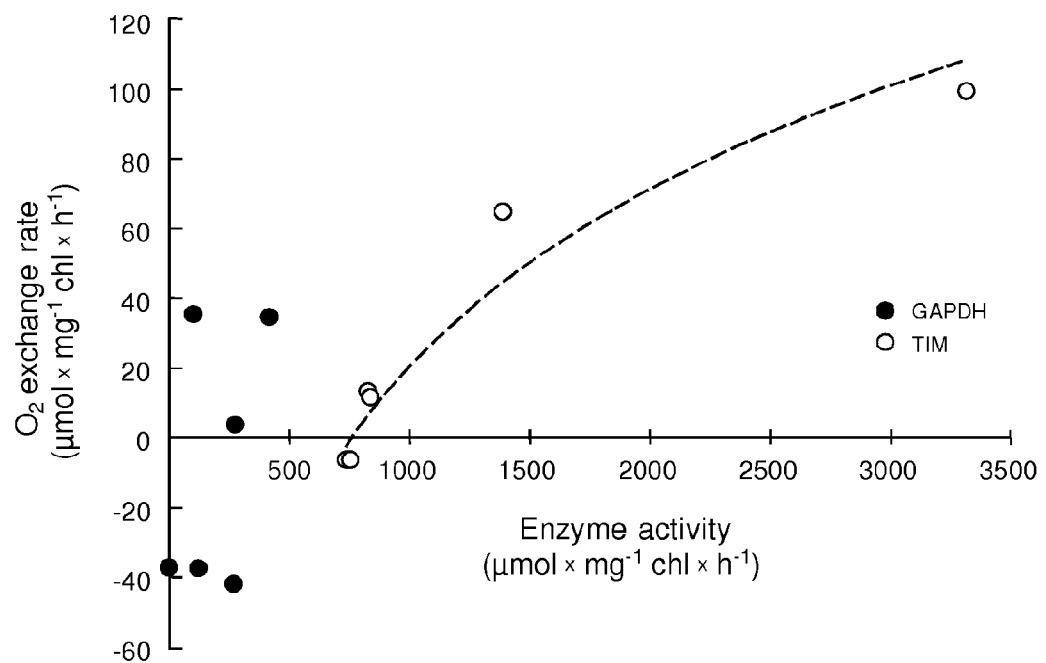
FIG. 6 shows the correlation between triose phosphate isomerase (TIM) and glyceraldehyde-3-phosphate dehydrogenase (GAPDH) activity rates and the $O_2$ exchange rate of Anabaena PCC 7120 spheroplasts treated with various concentrations of Ornidazole.

A clear correlation was found between the reduced activity of triose phosphate isomerase and the declined rate of photosynthesis. This enzyme was inhibited at lower concentrations of Ornidazole and in a concentration-dependent manner compared to GAPDH (FIG. 6).

As is shown hereinabove, Ornidazole inhibited photosynthesis in all examined photosynthetic organisms. The rate of photosynthesis of *Anabaena* spheroplasts treated with various concentrations of Ornidazole was correlated with the activities of GAPDH or triose phosphate isomerase extracted from the treated spheroplasts.

Example 4

Biodegradation of Ornidazole

The concentrations of Ornidazole and its degradation product in the medium were determined during the growth of the cyanobacterium *Anabaena* PCC7120 and in media lacking cyanobacteria in the dark or under illumination. Ornidazole at 0.1 mM concentration was added to three growth tubes containing BG-11 medium: one growth tube was kept in the dark, the second under light conditions of 60 μmol photons $m^{-2}$ $sec^{-1}$ and the third tube, to which *Anabaena* cells were added, was also kept under similar light conditions. Samples from each tube were taken every day, separated on a C18 reverse phase HPLC column, and Ornidazole (molecular mass 220 and 222 due to two isotopes of chlorine) or degradation products were sought by LC-MS. A degradation product of molecular mass 184, identified as $C_7H_9N_3O_3$, was found in all three tubes.

Figure 7A:
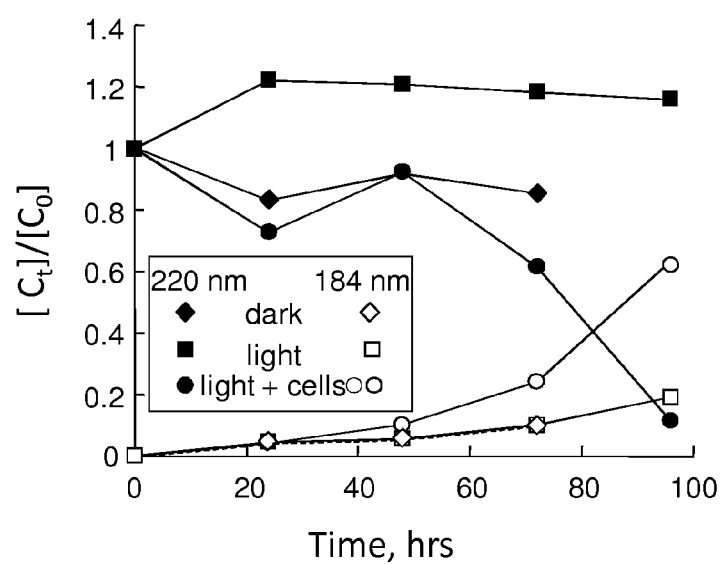
FIG. 7A-C demonstrates the stability of Ornidazole in a growth medium in the presence or absence of Anabaena cell, under normal light conditions or in the dark. Ornidazole (molecular mass 220 and 222 due to two isotopes of chlorine) or degradation products were sought by LC-MS. The chromatograms of samples from the first and fourth days are shown in FIG. 7B and FIG. 7C, respectively. The retention time and molecular mass of the isolated molecules are designated.
Figure 7B:
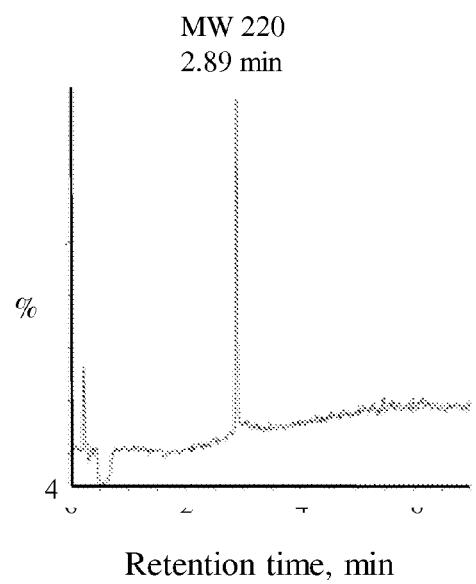
Figure 7C:
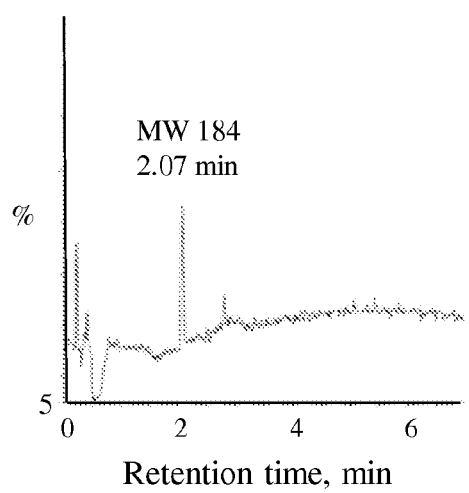

Whereas the Ornidazole concentration in medium lacking cells remained stable during four days, in the presence of cyanobacteria, Ornidazole degraded so that after four days of incubation only 10% of its initial concentration was measured. After seven days Ornidazole could no longer be detected. In parallel, a degradation product of Ornidazole formed by hydrolysis of the Chlorine atom appeared in the medium. This product appeared also in lower concentrations in media lacking cyanobacteria both under illumination or in the dark (FIG. 7). These findings indicate slow spontaneous hydrolysis of Ornidazole, which is accelerated in the presence of cyanobacteria.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method of inhibiting the growth of a photosynthetic organism, comprises applying to the photosynthetic organism and/or to its habitat where the photosynthetic organism is growing or will grow a compound or a plurality of compounds having the general formula I, or a salt thereof:

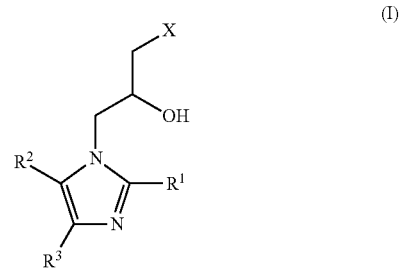

(I)

wherein:
$R^1$ is H, halogen or $C_1$-$C_4$ alkyl;
one of $R^2$ and $R^3$ is H or halogen and the other is $NO_2$; and
X is a halogen;
thereby inhibiting the growth of said photosynthetic organism, and
wherein said photosynthetic organism is selected from the group consisting of plants, algae and cyanobacteria.

2. The method of claim 1, wherein $R^1$ is $C_1$-$C_4$ alkyl.

3. The method of claim 1, wherein the halogen is selected from the group consisting of fluorine, chlorine, bromine and iodine.

4. The method of claim 1, wherein $R^1$ is methyl, $R^2$ is $NO_2$, $R^3$ is H and X is chlorine, said compound is Ornidazole, or a salt thereof.

5. The method of claim 1, wherein the photosynthetic organism is a plant selected from the group consisting of aquatic plants and terrestrial plants.

6. The method of claim 1, wherein the photosynthetic organism is algae selected from the group consisting of green algae and diatoms.

7. The method of claim 1, wherein the compound or the plurality of compounds having the general formula I is applied to the photosynthetic organism.

8. The method of claim 7, wherein the photosynthetic organism is a plant and wherein the compound or plurality of compounds having the general formula I are applied onto a plant part selected from the group consisting of roots, shoots, foliage, flowers, fruit, seeds or any portion thereof.

9. The method of claim 1, wherein the compound or the plurality of compounds having the general formula I is applied to the photosynthetic organism habitat.

10. The method of claim 9, wherein the photosynthetic organism habitat comprises a growth medium selected from the group consisting of natural soil, artificial soil, natural aqueous medium and artificial aqueous medium.

11. The method of claim 1, wherein the compound or the plurality of compounds having the general formula I is applied simultaneously to the photosynthetic organism and to said photosynthetic organism habitat.

12. The method of claim 1, wherein the compound or the plurality of compounds having the general formula I is applied at an amount sufficient to inhibit the growth of the photosynthetic organism.

13. The method of claim 5, wherein said compound is Ornidazole or a salt thereof.

14. The method of claim 6, wherein said compound is Ornidazole or a salt thereof.

15. The method of claim 8, wherein said compound is Ornidazole or a salt thereof.

16. A herbicidal composition to be applied to a photosynthetic organism and/or to its habitat where the photosynthetic organism is growing or will grow comprising (i) a compound or plurality of compounds having the general formula I, or a salt thereof:

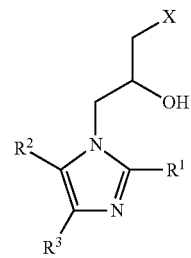

wherein:
$R^1$ is H, halogen or C1-C4 alkyl;
one of $R^2$ and $R^3$ is H or halogen and the other is $NO_2$; and
X is a halogen,
(ii) at least one additional active agent selected from the group consisting of fungicides, insecticides, additional herbicides, nematicides, acaricides, bactericides, plant growth regulators, fertilizers, soil improvers and a combination thereof, and
(iii) an agriculturally acceptable diluent or carrier wherein the herbicide composition is effective in inhibiting the growth of a photosynthetic organism and wherein the photosynthetic organism is selected from the group consisting of plants, algae and cyanobacteria.

17. The composition of claim 16, wherein $R^1$ is $C_1$-$C_4$ alkyl.

18. The composition of claim 16, wherein the halogen is selected from the group consisting of fluorine, chlorine, bromine and iodine.

19. The composition of claim 16, wherein $R^1$ is methyl, $R^2$ is $NO_2$, $R^3$ is H and X is chlorine, said compound is Ornidazole or a salt thereof.

20. The composition of claim 16, wherein said composition is formulated in a form selected from the group consisting of wettable powder, dusts, pastes, granule, powder, emulsion, solutions, water-soluble powder, suspension, aerosol and flowable composition impregnated with natural and synthetic substances and microencapsulated in polymeric substances.

* * * * *